US 6,544,756 B1

United States Patent
Uchida et al.

(10) Patent No.: US 6,544,756 B1
(45) Date of Patent: Apr. 8, 2003

(54) SORBITOL DEHYDROGENASE, MICROORGANISM FOR PRODUCING SAME, PROCESS FOR THE PRODUCTION THEREOF, METHOD FOR THE MEASUREMENT OF SORBITOL AND REAGENT FOR THE QUANTITATIVE DETERMINATION THEREFOR

(75) Inventors: Michie Uchida, Kyoto (JP); Ryoko Nakatani, Kyoto (JP); Keisuke Kurosaka, Kyoto (JP); Shido Kawase, Kyoto (JP); Miwa Watanabe, Kyoto (JP)

(73) Assignee: Unitika Ltd., Hyogo (JP)

(*) Notice: Subject to any disclaimer, the term of this patent is extended or adjusted under 35 U.S.C. 154(b) by 55 days.

(21) Appl. No.: 09/645,356

(22) Filed: Aug. 25, 2000

(30) Foreign Application Priority Data

Aug. 25, 1999 (JP) .......................... 11-238284

(51) Int. Cl.[7] .......................... C12Q 1/32; C12Q 1/00; C12N 9/00; C12N 1/20
(52) U.S. Cl. .......................... 435/26; 435/4; 435/183; 435/253.3; 435/850
(58) Field of Search .......................... 435/26, 4, 183, 435/253.3, 850

(56) References Cited

FOREIGN PATENT DOCUMENTS

JP        A-8-33482        2/1996

OTHER PUBLICATIONS

Stryer, Biochemistry, pp. 112–114, 1981.*

Ng et al, "Sorbitol Dehydrogenase from *Bacillus Subtilis*: Purification, Characterization, and Gene Cloning", Journal of Biological Chemistry, vol. 267, No. 35, 1992, pp. 24989–24994.

Burnell et al, "Purification and Properties of Sorbitol Dehydrogenase from Mouse Liver", International Journal of Biochemistry, vol. 15, No. 4, 1983, pp. 507–511.

XP–002151858, Abstract of Anzai Yojiro et al article in Internationa Journal of Systematic Biology (1997).

European Search Report (Nov. 3, 2000).

* cited by examiner

*Primary Examiner*—Louise N. Leary
(74) *Attorney, Agent, or Firm*—Sughrue Mion, PLLC

(57) ABSTRACT

A novel sorbitol dehydrogenase having excellent substrate affinity and substrate specificity which can be used to measure D-sorbitol which occurs in human erythrocytes and serum in a slight amount or D-sorbitol or D-fructose contained in foods, a microorganism for producing such an enzyme, and a process for the production of the enzyme using such a microorganism. Also disclosed is provides a method for the measurement of sorbitol using the foregoing sorbitol dehydrogenase and a reagent for the quantitative determination therefor.

9 Claims, 8 Drawing Sheets

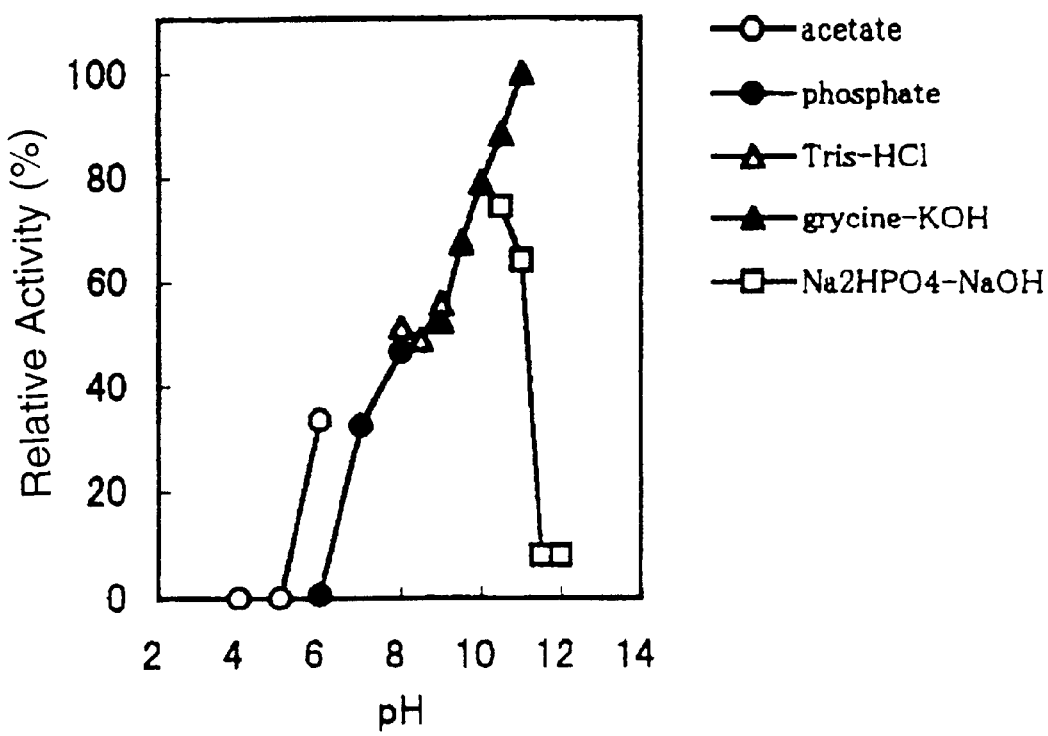
FIG 3  A-989
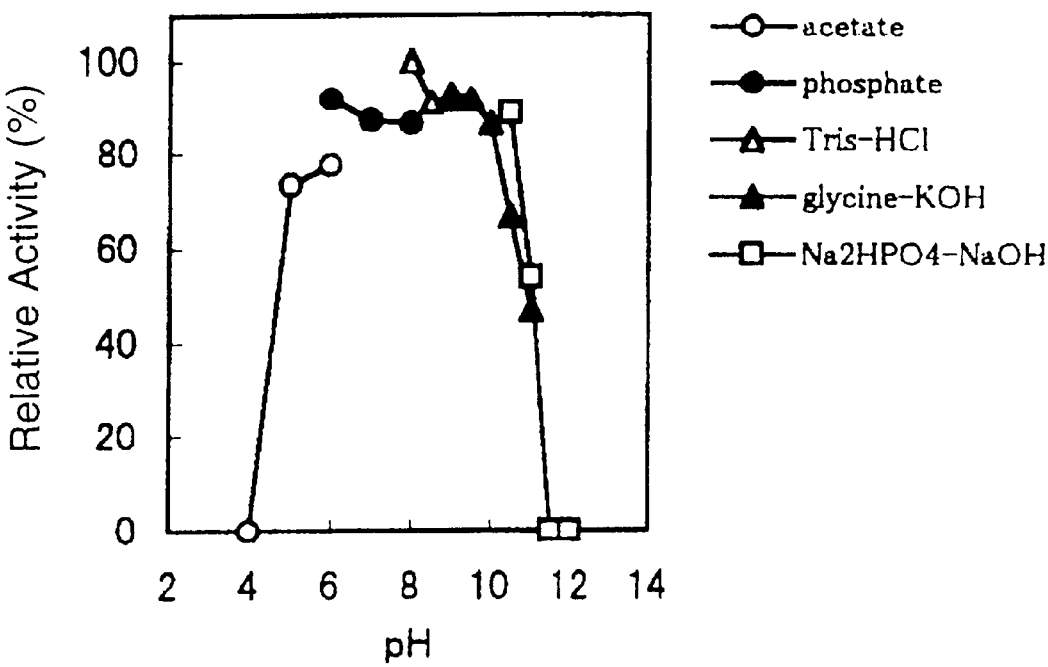
FIG 4  A-520

FIG 5  A-654
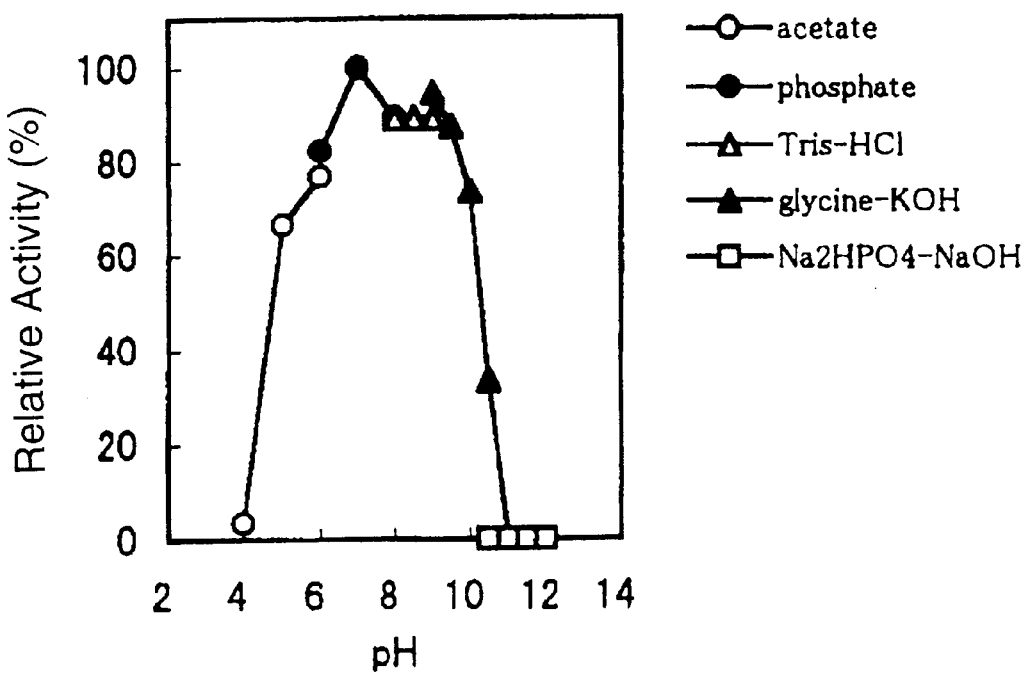
FIG 6  A-989
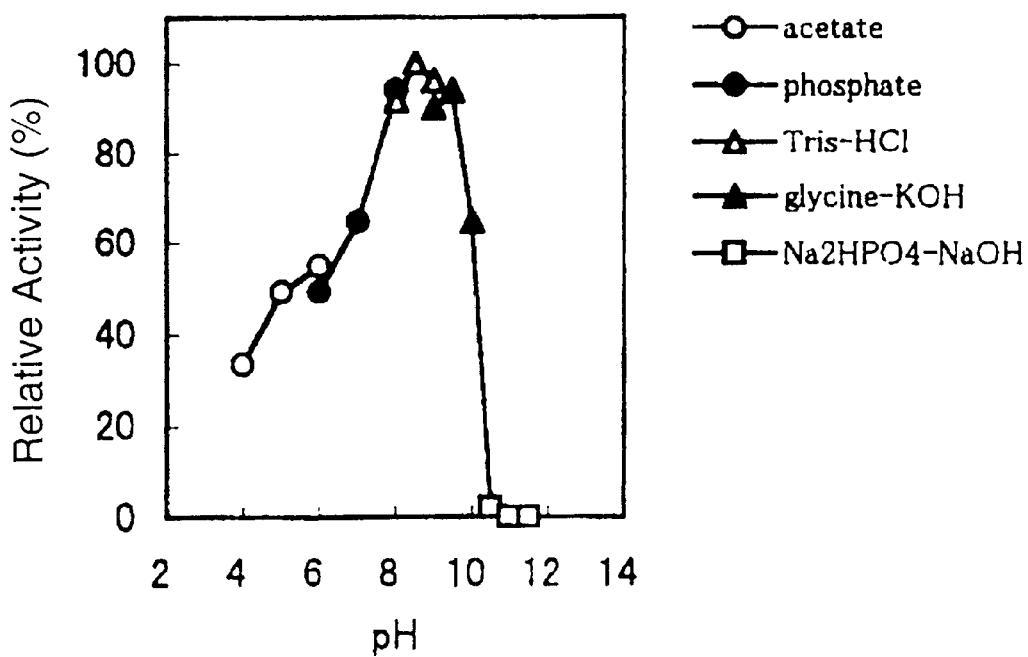

A-520

A-654

FIG 9    A-989
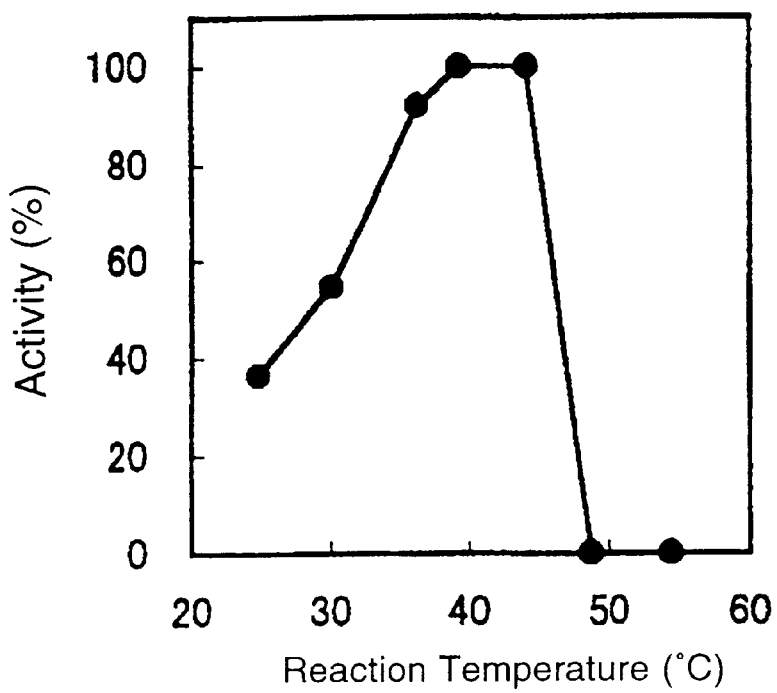
FIG 10   A-520
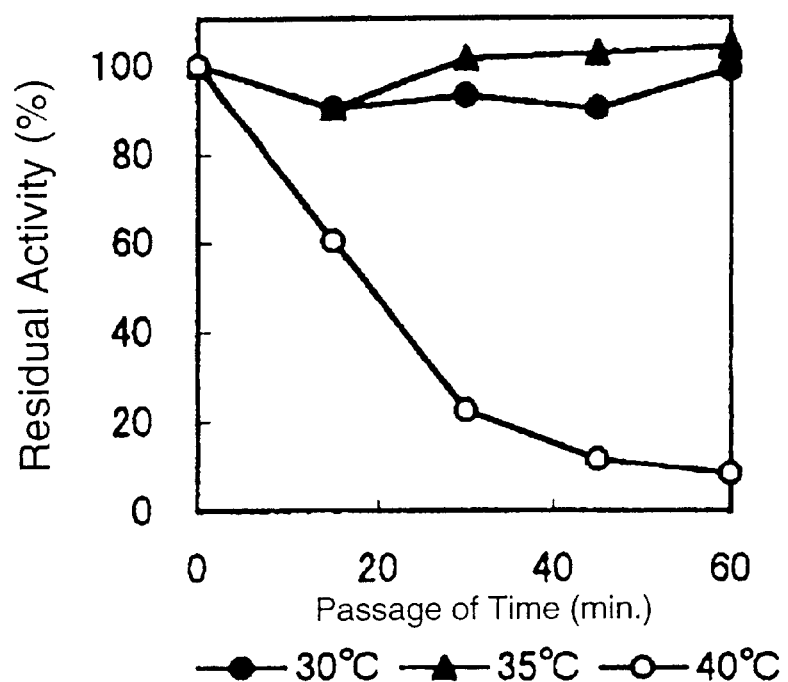

FIG 11  A-654
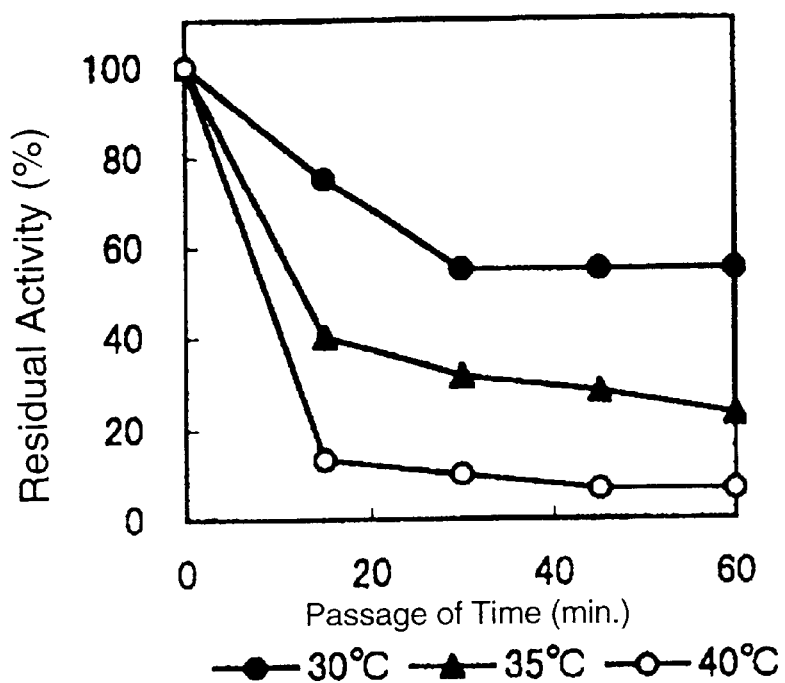
FIG 12  A-989
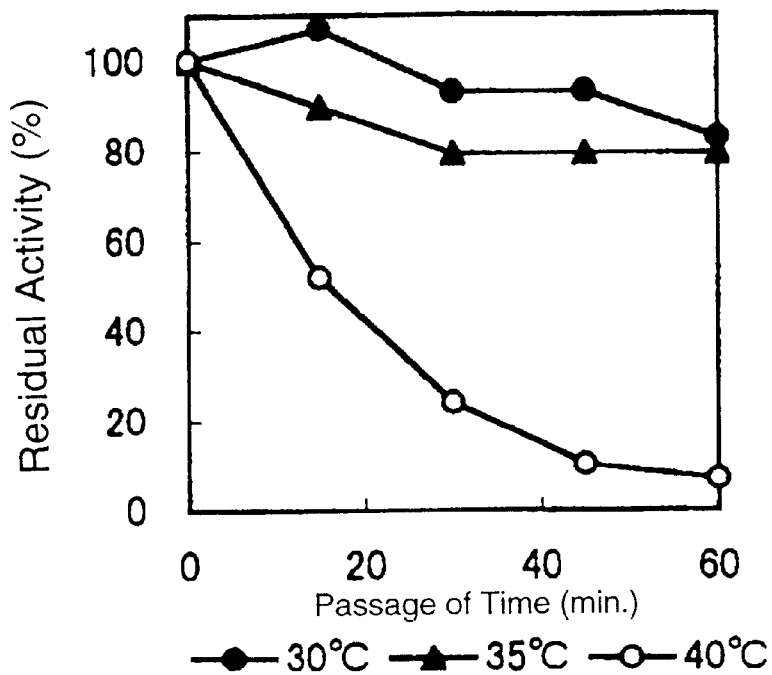

SORBITOL DEHYDROGENASE, MICROORGANISM FOR PRODUCING SAME, PROCESS FOR THE PRODUCTION THEREOF, METHOD FOR THE MEASUREMENT OF SORBITOL AND REAGENT FOR THE QUANTITATIVE DETERMINATION THEREFOR

FIELD OF THE INVENTION

The present invention relates to a novel sorbitol dehydrogenase, a microorganism for producing such an enzyme and a process for the production of a sorbitol dehydrogenase using the same. More particularly, the present invention relates to a sorbitol dehydrogenase which acts on sorbitol with high sensitivity and high selectivity, a microorganism for producing such an enzyme and a process for the production of a sorbitol dehydrogenase using the same. The present invention further relates to a method for the measurement of sorbitol using the foregoing sorbitol dehydrogenase and a reagent for the quantitative determination therefor.

BACKGROUND OF THE INVENTION

D-Sorbitol is a compound which occurs in human erythrocytes and serum in a slight amount. It is known that the content of D-sorbitol is an important indication of certain diseases, particularly diabetes. It is reported that D-sorbitol is useful as a diagnostic marker for diabetes.

D-sorbitol and D-fructose have long been widely used as sweetening agents in the food industry.

Examples of the process for the measurement of sorbitol include a process involving gas chromatography, a process involving liquid chromatography, and a process involving the use of an enzyme. However, both the process involving gas chromatography and the process involving liquid chromatography require a complicated operation so that it is difficult to treat a large amount of test samples.

The process involving the use of an enzyme comprises the oxidation of D-sorbitol with a sorbitol dehydrogenase (EC 1.1.1.14) in the presence of $NAD^+$, wherein the amount of $NAD^+$ reduced to NADH is measured based on fluorescent intensity. This method can be easily applied to automatic analyzers and presently finds widest application.

Examples of sorbitol dehydrogenases which have heretofore been known include those derived from animal liver such as sorbitol dehydrogenase derived from sheep liver available from Rosch Inc., and those derived from microorganisms such as an enzyme derived from Pseudomonas sp. described in "Enzyme Microb. Technol.", vol. 13, pp. 332–337, April, 1991, an enzyme derived from *Bacillus subtilis* described in "Journal of Biological Chemistry", vol. 267, No. 35, pp. 24,989–24,994, 1992, an enzyme derived from Pseudomonas sp. described in "Journal of Fermentation and Bioengineering", vol. 84, No. 3, pp. 254–256, 1997, and JP-08-033482, and an enzyme derived from Bacillus fructose described in "Biosci. Biotechnol. Biochem.", vol. 63, No. 3, pp. 573–574, 1999.

However, the foregoing sorbitol dehydrogenases are disadvantageous in that they have a low substrate specificity and a high Km with respect to sorbitol. In other words, the foregoing sorbitol dehydrogenases derived from animal liver, sorbitol dehydrogenases derived from *Bacillus subtilis*, and sorbitol dehydrogenases derived from Pseudomonas sp. show almost the same reactivity to iditol, iditol and xylitol, and galactitol, respectively, as sorbitol. Further, all the foregoing sorbitol dehydrogenases exhibits a Km of about 10 mM or more with respect to sorbitol, which presents difficulties in the measurement of sorbitol.

On the other hand, the sorbitol dehydrogenases disclosed in JP-56-029994, U.S. Pat. No. 5,747,301, EP-728840, WO 99/20763, EP-897984 and KR-98069057 are enzymes which produce sorbose with sorbitol as a substrate and thus are different from the enzyme of the present invention.

Further, JP-06-209793, JP-06-189790, JP-01-08692, U.S. Pat. No. 5,250,420, WO 92/21775, JP-07-322897, and JP-06-109726 disclose a process for the measurement of sorbitol using a sorbitol dehydrogenase. However, JP-06-209793 and JP-06-189790 concern a process for the measurement of sorbitol using the enzyme disclosed in the above cited JP-56-029994; JP-10-108692 concerns a process for the measurement of sorbitol using the enzyme disclosed in the above cited JP-08-033482; and U.S. Pat. No. 5,250,420, WO 92/21775, JP-07-322897, and JP-06-109726 concern a process for the measurement of sorbitol using a commercially available enzyme. None of these references describes the enzyme disclosed.

Moreover, the following references describe sorbitol dehydrogenases, but none of them describes the enzyme disclosed herein. That is, EP-524517, EP-791355, WO 94/07867, U.S. Pat. No. 5,998,463, SU-1553897, WO 98/33936, and SU-1567626 refer to sorbitol dehydrogenases derived from the human body concerning the treatment of diabetes. The sorbitol dehydrogenases to be used in the processes disclosed in JP-09-037796, JP-63-146800, JP-61-005091, JP-9-2066875, and DE-3326546 are enzymes the origin of which is not specified or which are commercially available. SU-1303937 refers to a sorbitol dehydrogenase derived from tea leaves. WO 94/15942 refers to a sorbitol dehydrogenase derived from yeast. DE-2022280 discloses a process for the measurement of xylitol. All of these are quite different from the enzyme of the present invention.

SUMMARY OF THE INVENTION

It is therefore an object of the present invention to provide a novel sorbitol dehydrogenase having excellent substrate affinity and substrate specificity which can be used to measure D-sorbitol which occurs in human erythrocytes and serum in a slight amount or D-sorbitol or D-fructose contained in foods, a microorganism for producing such an enzyme, and a process for the easy production of the enzyme using such a microorganism.

The inventors made extensive studies to solve these problems. As a result, they found that a microorganism belonging to Flavimonas and Pseudomonas separated from the soil produces a sorbitol dehydrogenase having excellent substrate affinity and substrate specificity. Thus, the present invention has been accomplished.

A first aspect of the present invention is directed to a sorbitol dehydrogenase having the following physicochemical properties.

(1) activity: the sorbitol dehydrogenase catalyzes dehydrogenation oxidation of D-sorbitol in the presence of $NAD^+$ to produce D-fructose, and catalyzes a reverse reaction which reduces D-fructose in the presence of NADH to produce D-sorbitol and $NAD^+$;

(2) substrate specificity: the sorbitol dehydrogenase exhibits a Vmax/Km value of about 40 or less for galactitol and about 3 or less for L-iditol when the Vmax/Km value for D-sorbitol is taken as 100, and which does not act on D-arabitol, D-mannitol, xylitol and D-glucose; and (3) exhibits a Km value of about 6 mM or less (preferably 4 mM or less) with respect to D-sorbitol.

A second aspect of the present invention is directed, to a microorganism belonging to Flavimonas or Pseudomonas capable of producing the foregoing sorbitol dehydrogenase.:

A third aspect of the present invention is directed to a process for the production of a sorbitol dehydrogenase, which comprises culturing the foregoing microorganism capable of producing a sorbitol dehydrogenase in a culture medium, and then collecting sorbitol dehydrogenase from the culture medium.

A fourth aspect of the present invention is directed to a process for the measurement of sorbitol, which comprises adding a composition containing the foregoing sorbitol dehydrogenase to a sample to cause a reaction, and then measuring the content of sorbitol in the sample.

A fifth aspect of the present invention is directed to a reagent for the quantitative determination of sorbitol comprising the foregoing sorbitol dehydrogenase, $NAD^+$ and a buffer.

The sorbitol dehydrogenase of the invention has excellent substrate specificity and substrate affinity, and thus is useful for the measurement of sorbitol.

BRIEF DESCRIPTION OF THE DRAWINGS

FIG. 3 is a graph illustrating the optimum pH value of a sorbitol dehydrogenase derived from A-989 strain at 30° C.;

FIG. 4 is a graph illustrating the stable pH value of the sorbitol dehydrogenase derived from A-520 strain at 4° C.;

FIG. 5 is a graph illustrating the stable pH value of the sorbitol dehydrogenase derived from A-654 strain at 4° C.;

FIG. 6 is a graph illustrating the stable pH value of the sorbitol dehydrogenase derived from A-989 strain at 4° C.;

FIG. 9 is a graph illustrating the optimum acting temperature of the sorbitol dehydrogenase derived from A-989 strain at pH 8.0;

FIG. 10 is a graph illustrating the thermal stability of the sorbitol dehydrogenase derived from A-520 strain at pH 8.0;

FIG. 11 is a graph illustrating the thermal stability of the sorbitol dehydrogenase derived from A-654 strain at pH 8.0;

FIG. 12 is a graph illustrating the thermal stability of the sorbitol dehydrogenase derived from A-989 strain at pH 8.0;

DETAILED DESCRIPTION OF THE INVENTION

Figure 1:
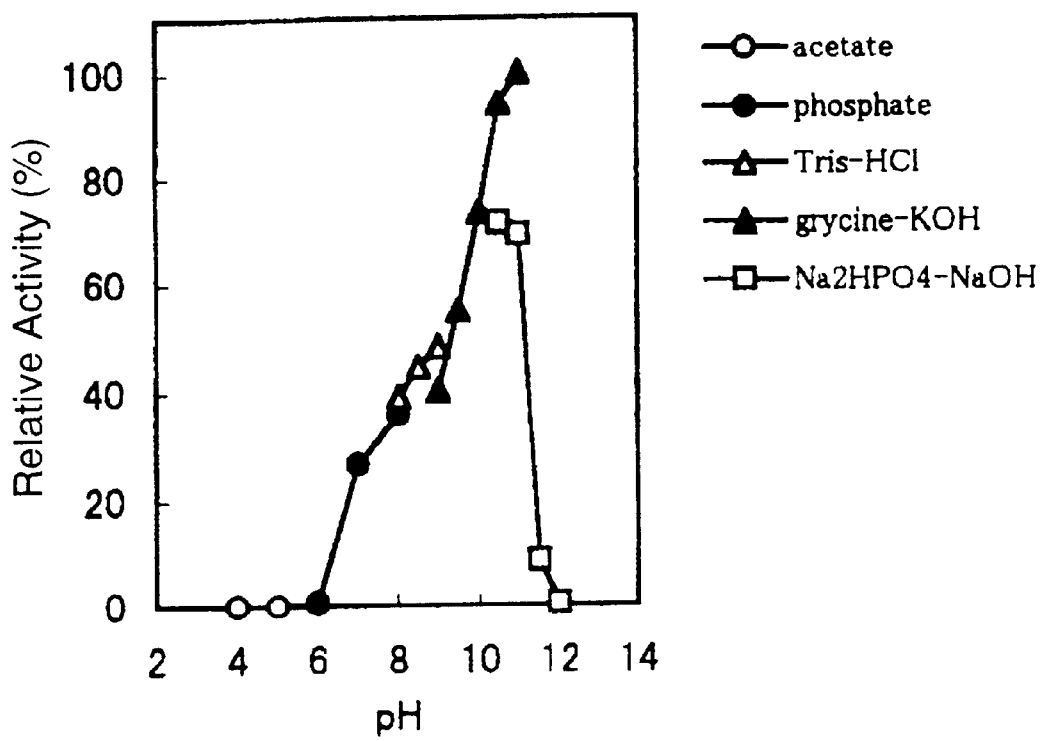
FIG. 1 is a graph illustrating the optimum pH value of a sorbitol dehydrogenase derived from A-520 strain at 30° C.

The present invention will be further described hereinafter.

The sorbitol dehydrogenase of the invention has the foregoing physicochemical properties. In the present invention, the measurement of the activity of sorbitol dehydrogenase was carried out by adding an enzyme solution to a 80 mM Tris-HCl buffer (pH 9.0) containing 50 mM of D-sorbitol and 2 mM of $NAD^+$, slowly mixing them, and then measuring the change of absorbance at 340 nm by means of a spectrophotometer. The measurement was made at a temperature of 30° C. The amount of enzyme required to produce 1 μmol of NADH per minute was defined to be 1 unit (U).

From natural sources, the present inventors isolated three strains capable of forming the enzyme of the present invention, and measured their mycological properties shown below.

TABLE 1

| Properties tested | Type of strain | | |
|---|---|---|---|
| | A-520 | A-989 | A-654 |
| Morphology | rod | rod | rod |
| Gram staining | − | − | − |
| Spore | − | − | − |
| Motility | + | + | + |
| Flagellum | Polar (=1) | Polar (>2) | Polar (>2) |
| Behavior to oxygen | Aerobic | Aerobic | Aerobic |
| Oxidase | − | + | + |
| Catalase | + | + | + |
| OF | o | o | o |
| Growth on McConkey's agar | + | + | + |
| Growth on SS agar | + | + | + |
| Growth on cetrimide agar | − | + | + |
| Growth on KCN medium | − | − | + |
| Use of citric acid | + | + | + |
| Hydrolysis of casein | − | + | + |
| Hydrolysis of gelatin | − | + | + |
| Hydrolysis of starch | − | + | + |
| Reduction of nitrate | − | + | − |
| Gas (nitrate) | − | + | − |
| Urease | − | − | − |
| Lysine decarboxylase | − | − | − |
| Arginine dehydrase | − | + | + |
| Ornithine decarboxylase | − | − | − |
| ONPG | − | − | − |
| LV | − | + | − |
| Lipase | − | − | − |
| Hydrolysis of esculin | − | − | − |
| Indole | − | − | − |
| DNase | − | − | + |
| Acetamide | − | − | − |
| Production of glucan | Not tested | + | + |
| Growth at 42° C. | − | − | − |
| Production of acid from carbohydrate | | | |
| Fructose | + | + | + |
| Trehalose | + | + | + |
| Xylose | + | + | + |
| Mannitol | + | + | + |
| Cellobiose | − | − | − |
| Lactose | − | − | − |
| Maltose | + | − | − |
| Glucose | + | + | + |
| Erythritol | − | − | − |
| Inositol | + | + | + |
| Sucrose | − | + | + |
| Salicin | − | − | − |

Using the foregoing mycological properties, search was made in Bargey's Manual of Systematic Bacteriology. As a result, A-520 strain, A-989 strain and A-654 strain were found to be a bacterium belonging to *Flavimonas oryzihabitans, Pseudomonas fluorescens*, and *Pseudomonas fluorescens*, respectively. *Flavimonas oryzihabitans* A-520 strain, *Pseudomonas fluorescens* A-989 strain and *Pseudomonas fluorescens* A-654 strain were respectively deposited with National Institute of Bioscience and Human Technology, Ministry of International Trade and Industry on Jul. 13, 1999 with Accession No. FERM P-17461, FERM P-17462 and FERM P-17463 (*Flavimonas oryzihabitans* A-520 strain was transferred to international deposition on Jun. 26, 2000; FERM BP-7195).

The microorganism which produces such a sorbitol dehydrogenase is not particularly limited, and preferably includes those belonging to the genus Flavimonas and the genus Pseudomonas. Preferred microorganisms include microorganisms belonging to *Flavimonas oryzihabitans* and *Pseudomonas fluorescens*, particularly *Flavimonas oryzihabitans* A-520 strain, *Pseudomonas fluorescens* A-989 strain and *Pseudomonas fluorescens* A-654 strain, and most preferably *Flavimonas oryzihabitans* A-520 strain.

It is possible for one skilled in the art to screen and isolate other microorganisms which are capable of producing the enzyme of the present invention, including allelic variants of the sorbitol dehydrogenases derived from *Flavimonas oryzihabitans* A-520 strain, *Pseudomonas fluorescens* A-989 strain and *Pseudomonas fluorescens* A-654 strain having similar physicochemical properties.

A microorganism capable of producing the enzyme of the present invention can be screened, for example, in the following manner. That is, a natural source such as soil is spread and cultured on an agar plate medium containing sorbitol as a sole carbon source. A colony formed on the medium is isolated and subjected to the culturing for the production of the enzyme. Then, sorbitol dehydrogenase is purified from the strain and the physicochemical properties are determined by the method described above. The strain which is capable of producing sorbitol dehydrogenase satisfying the physicochemical properties of the present invention is selected.

The sorbitol dehydrogenase of the present invention may be obtained from these microorganisms as follows. The microorganism is cultured in a culture medium. The culture medium is then subjected to centrifugal separation or filtration to collect bacterium cells. Subsequently, the bacterium is extracted to obtain a crude enzyme solution which is then purified.

The carbon source to be incorporated in the culture medium for use in the culture of such a microorganism may be any carbon source which can be assimilated by the microorganism. In practice, D-sorbitol, glucose, fructose, maltose, sucrose, glycerol, succinic acid, lactose, etc., may be used. The nitrogen source for use in the culture medium may be an inorganic nitrogen compound such as ammonium sulfate and ammonium chloride or an organic nitrogen compound such as peptone, meat extract, yeast extract, casamino acids and corn steep liquor. An inorganic salt to be added to the culture medium may be a salt of potassium, sodium, zinc, iron, magnesium or manganese. As necessary, a slight amount of metal salt, vitamins, anti-foaming agent, etc., may be added.

In the present invention, sorbitol, which is a substrate, is preferably added to the culture medium as an enzyme production accelerator at any time during culture to effect the production of the sorbitol dehydrogenase more efficiently.

Any of solid culture and liquid culture may be employed. In practice, aerated agitated culture or shaken culture is desirable. The culture medium is preferably adjusted to a pH of from about 6 to 8. The culture is effected at a temperature of from 18° C. to 42° C., preferably from 25° C. to 35° C. The culture time may be such that the enzyme can be produced at maximum. In practice, however, it is from 10 hours to 100 hours, preferably from 20 hours to 70 hours. In this manner, the sorbitol dehydrogenase is produced and accumulated in the bacterium.

The extraction of the enzyme from the bacterium thus obtained can be accomplished by self digestion, ultrasonic destruction, French Press, treatment with surface active agent, treatment with lysozyme, etc. The bacterium thus treated is then subjected to centrifugal separation or the like to remove cell fragments. Thus, a crude enzyme solution is obtained.

The crude enzyme solution thus obtained is then subjected to an appropriate combination of chromatography techniques such as ion exchange chromatography, affinity chromatography, hydrophobic chromatography and gel permeation chromatography in combination so that it is purified into the sorbitol dehydrogenase of the invention. Examples of the ion exchange resin employable herein include Q-Sepharose FF (produced by Pharmacia Corporation), and DEAE-Sepharose (produced by Pharmacia Corporation). Examples of the resin for affinity chromatography employable herein include resins prepared from triazine dye, such as Blue Sepharose CL-6B and Red Sepharose CL-6B (produced by Pharmacia Corporation), Prussian Blue H-ERD (produced by ICI Inc.) and Chiba Chrome Yellow HE-3G (produced by Ciba Geigy Inc.). Examples of the resin for hydrophobic chromatography employable herein include Octyl-Sepharose CL-4B (produced by Pharmacia Corporation). Examples of the carrier or resin for gel permeation chromatography employable herein include Cephadex G-100. In addition to these column chromatographies, the removal of nucleic acid involving treatment with streptomycin sulfate or protamine sulfate or salting-out of protein involving treatment with ammonium sulfate may be employed.

The physicochemical properties of the sorbitol dehydrogenase of the invention thus produced will be given below.

(1) Activity: The inventive sorbitol dehydrogenase catalyzes dehydrogenation oxidation of D-sorbitol in the presence of $NAD^+$ to produce D-fructose, and also catalyzes the reverse reaction which reduces D-fructose in the presence of NADH to produce D-sorbitol and $NAD^+$.

(2) Substrate specificity: The Vmax/Km of the sorbitol dehydrogenase of the invention with respect to various substrates (relative to that with respect to D-sorbitol taken as 100) is about 40 or less for galactitol and about 3 or less for iditol, preferably about 30 or less for galactitol and about 2 or less for iditol. The Km for D-sorbitol is about 6 mM or less, preferably about 4 mM or less. Among the sorbitol dehydrogenases of the invention, the substrate specificities of those derived from *Flavimonas oryzihabitans* A-520 strain, *Pseudomonas fluorescens* A-989 strain and *Pseudomonas fluorescens* A-654 strain are shown in Table 2 below.

Definitions of Vmax and Km:

Vmax means the maximum velocity of the reaction at the saturated substrate concentration and Km means the Michaelis constant. The Vmax/Km values indicates the apparent binding constant of the enzyme reaction as a whole, which is generally used as an index for reflecting the substrate specificity. These values may be measured and calculated in accordance with the methods described in Chapter 8 of *Biochemistry*, second edition, by Albert Lehninger, 1975, Worth Publishers, Inc. or in *Enzyme Structure and Mechanism*, second edition, by Alan Fersht, 1984, W. H. Freeman & Co.

TABLE 2

|  | Flavimonas oryzihabitans A-520 | | Pseudomonas fluorescens A-989 | | Pseudamonas fluorescens A-654 | |
| --- | --- | --- | --- | --- | --- | --- |
|  | Vmax/Km (%) | Km (mM) | Vmax/Km (%) | Km (mM) | Vmax/Km (%) | Km (mM) |
| Sorbitol | 100 | 2.5 | 100 | 5.9 | 100 | 3.5 |
| Galactitol | 28.9 | 1.9 | 36.8 | 3.1 | 31.9 | 2.0 |
| Iditol | 1.99 | 112.3 | 2.78 | 139.0 | 1.55 | 197.6 |
| Arbitol | 0 | — | 0 | — | 0 | — |
| Mannitol | 0 | — | 0 | — | 0 | — |
| Xylitol | 0 | — | 0 | — | 0 | — |
| D-Glucose | 0 | — | 0 | — | 0 | — |

Figure 2:
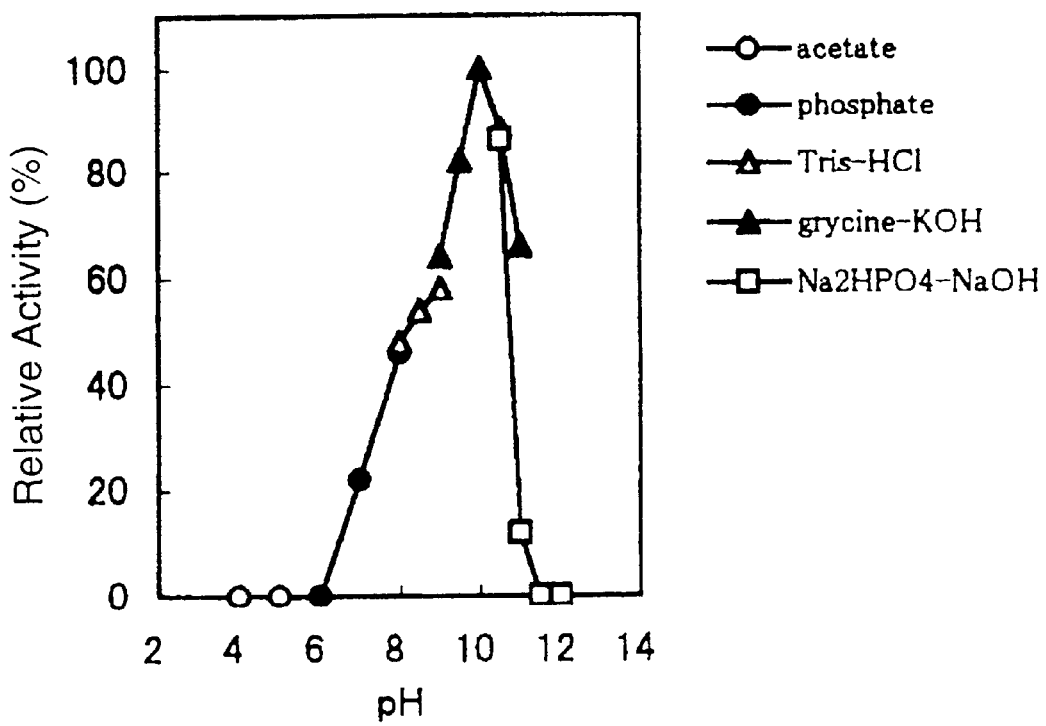
FIG. 2 is a graph illustrating the optimum pH value of a sorbitol dehydrogenase derived from A-654 strain at 30° C.

(3) Optimum pH: The enzyme of the present invention has an optical pH range of from about 9.5 to about 11, preferably from about 10 to about 11. Among the sorbitol dehydrogenases of the present invention, the optimum pH values of the sorbitol dehydrogenases derived from *Flavimonas oryzihabitans* A-520 strain, *Pseudomonas fluorescens* A-989 strain and *Pseudomonas fluorescens* A-654 strain are from 10 to 11, from 10 to 11, and from 9.5 to 10.5, respectively. FIGS. 1 to 3 are graphs illustrating the effect of pH on the activity of the enzyme of the invention wherein the ordinate indicates the enzyme activity and the abscissa indicates pH. The activity of the enzyme is represented relative to the maximum measured value taken as 100. The buffers that were used for the measurements were a 100 mM acetate buffer for the pH range of from 4 to 6, a 100 mM potassium phosphate buffer for the pH range of from 6 to 8, a 100 mM Tris-HCl buffer for the pH range of from 8 to 9, a 100 mM glycine-potassium hydroxide buffer for the pH range of from 9 to 11 and a 100 mM disodium phosphate-sodium hydroxide buffer for the pH range of from 10.5 to 12.

(4) pH stability: When the enzyme of the present invention is allowed to stand at a temperature of 4° C. in buffers having various pH values for 24 hours, 60% residual activity is maintained in the pH range of from about 5 to about 10.5. Among the sorbitol dehydrogenases of the invention, the pH ranges where the sorbitol dehydrogenases derived from *Flavimonas oryzihabitans* A-520 strain, *Pseudomonas fluorescens* A-989 strain and *Pseudomonas fluorescens* A-654 strain were kept active in a proportion of 60% or more of the initial value were from 5 to 10.5, 7 to 10, and 5 to 10, respectively.

FIGS. 4 to 6 are graphs illustrating the effect of pH on the stability of the enzyme of the invention where the ordinate indicates the residual activity and the abscissa indicates pH. The residual activity is represented relative to the maximum measured value taken as 100. The buffers that were used for the measurements were a 100 mM acetate buffer for the pH range of from 4 to 6, a 100 mM potassium phosphate buffer for the pH range of from 6 to 8, a 100 mM Tris-HCl buffer for the pH range of from 8 to 9, a 100 mM glycine-potassium hydroxide buffer for the pH range of from 9 to 11 and a 100 mM disodium phosphate-sodium hydroxide buffer for the pH range of from 10.5 to 12.

(5) Optimum temperature and thermal stability: The optimum temperature of the sorbitol dehydrogenases of the invention is around 40° C. and the activity is maintained even after 1 hour of treatment at pH 8.0 and 35° C. Among the sorbitol dehydrogenases of the invention, those derived from *Flavimonas oryzihabitans* A-520 strain and *Pseudomonas fluorescens* A-989 strain remained active in a proportion of 80% or more of the initial value even after 1 hour of treatment at pH 8.0 and 35° C. The sorbitol dehydrogenase derived from *Pseudomonas fluorescens* A-654 strain remained active in a proportion of 60% or more of the initial value even after 1 hour of treatment at pH 8.0and 30° C.

Figure 7:
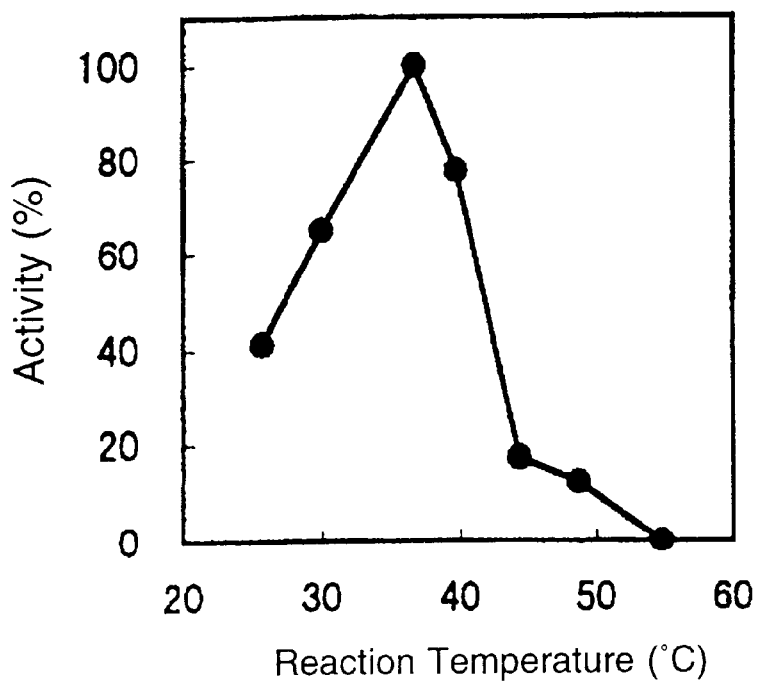
FIG. 7 is a graph illustrating the optimum acting temperature of the sorbitol dehydrogenase derived from A-520 strain at pH 8.0.
Figure 8:
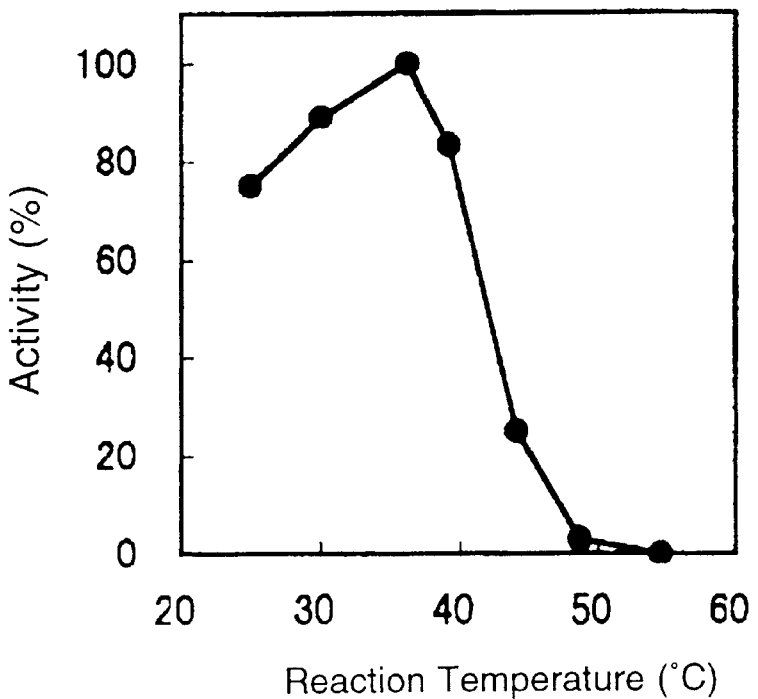
FIG. 8 is a graph illustrating the optimum acting temperature of the sorbitol dehydrogenase derived from A-654 strain at pH 8.0.

FIGS. 7 to 9 are graphs illustrating the effect of temperature on the activity of the enzyme of the invention, where the ordinate indicates the enzyme activity and the abscissa indicates temperature. The enzyme activity is represented relative to the maximum measured value taken as 100. FIGS. 10 to 12 are graphs illustrating the effect of temperature on the stability of the enzyme of the invention, where the ordinate indicates the residual activity and the abscissa indicates elapsed time. The residual activity is represented relative to the activity measured at the beginning of incubation taken as 100.

(6) Molecular weight: The molecular weights of the sorbitol dehydrogenases of the invention are in the range of from about 68,000 to about 38,000 and the molecular weights of the subunits are within the range of from about 26,000 to about 28,000. Among the sorbitol dehydrogenases of the present invention, the molecular weights of those derived from *Flavimonas oryzihabitans* A-520 strain, *Pseudomonas fluorescens* A-989 strain and *Pseudomonas fluorescens* A-654 strain as determined by gel permeation chromatography with Superose (produced by Pharmacia Corporation) are about 68,000, about 38,000 and about 52,000, respectively. The molecular weights of the subunit determined by SDS-PAGE method are about 26,000, about 26,000 and about 28,000, respectively.

The enzyme of the invention is extremely useful for the quantitative determination of D-sorbitol and a trace amount of D-sorbitol can be precisely determined by the use of the enzyme of the invention.

Diabetes is a disease where a high blood sugar level is maintained without subjective symptom based on various factors and results in diabetic complications showing serious symptoms. On the other hand, the cells such as mesangial cells in kidneys, retinal cells, neuronal cells, erythrocytes, etc. that receive passive inflow of glucose into the cells without participation of insulin has a sorbitol metabolizing pathway, which metabolizes glucose to sorbitol and then to fructose for the efflux out of the cells. When the amount of glucose inflow into such cells is increased under the high blood sugar level by diabetes, the activity of aldose reducatase, which reduces glucose into sorbitol, is accelerated and the intracellular sorbitol level is increased. However, the activity of sorbitol dehyrogenase, which reduces sorbitol to fructose, is not increased, sorbitol is not metabolized rapidly and sorbitol is accumulated in cells. Such condition is called "polyol metabolism disorder".

Because of the intracellular sorbitol accumulation in the polyol metabolism disorder, the intracellular osmotic pressure increases. As a result, moisture flows into the cells and the cells swell, which causes functional disorders of cells and becomes a factor for diabetic complications such as diabetic retinopathy, diabetic nephropathy, and diabetic neuropathy. The polyol metabolism disorder is treated with a drug such as aldose reductase inhibitor (ARI) which inhibits metabolism from glucose to sorbitol.

Therefore, in vivo measurement of sorbitol concentration in erythrocytes is effective for monitoring the conditions of prevention and/or treatment of these complications.

Sorbitol exists in vivo in an extremely low amount and various substances which are analogous to sorbitol exist. Accordingly, use of an enzyme having a high specificity and a high affinity for sorbitol is required for the measurements of a trance amount of sorbitol in a short period of time.

The sorbitol concentration in erythrocytes is about 4 $\mu$M in the case of normal human but can become about 17 $\mu$M in the high blood sugar condition. Because the test sample is generally used in an amount of about 10% of the measurement solution, it is required that at least the range of from 0.4 $\mu$M to 1.7 $\mu$M of sorbitol in the measurement solution should be determined.

By the use of the enzyme of the invention, it is possible to quantitatively determine from 0.025 $\mu$M to 8 $\mu$M of D-sorbitol in the reaction solution within 3 minutes, which is quite useful for the monitoring of the conditions of the diabetic complications.

The reagent for the quantitative determination of D-sorbitol according to the present invention comprises the enzyme of the invention and an electron acceptor as essential components. The electron acceptor for use is not specifically limited as long as it can cause dehydrogenic oxidation of D-sorbitol. $NAD^+$, oxygen, phenanzine methoxysulfate, dichlorophenol indophenol, potassium ferricyanate and sodium ferricyanate, chitochromium C, $NADP^+$, FMN, and the like coenzymes may be used. The concentration of D-sorbitol in a sample may be determined by determining the amount of the reduced coenzyme formed by the reaction by the invention enzyme based on change in the absorbance or fluorescence intensity as an index. When $NAD^+$ or $NADP^+$ is used as an electron acceptor, quantitative determination may also be carried out by using a dye (e.g., a tetrazolium salt such as nitroblue tetrazolium or 2,6-dichlorophenol indophenol) and an enzyme which catalyzes reduction of the dye using NADH or NADPH as a substrate in addition to the above-described essential components, and allowing measurement of the colored reduced dye in the visible range.

The buffers used for the reagent for the quantitative determination of D-sorbitol according to the invention is not particularly limited as long as the buffer has a sufficient buffering ability at the pH where the enzyme of the invention is stable and maintains good activity. Examples of the buffer include potassium phosphate, Tris, etc.

The reagent for the quantitative determination of D-sorbitol may further include various other additives as long as the object of the present invention is not impaired. Examples of the additives include metal chelating agents, surfactants, reducing agents, stabilizers, dissolution aids, which may be used either alone or in combination.

Preferable examples of the reagent for the quantitative determination of sorbitol include a solution (pH 8.5 to 10.5) containing 0.5 to 10 unit/ml of the invention enzyme, 1 to 5 mM $NAD^+$, and 10 to 200 mM buffer. Another preferable examples of the reagent includes the same solution but may further contain 1 to 10 unit/ml Diaphorase-I (Unitika Ltd.) and 0.5 to 5 mM WST-8 (Dojindo).

The reagent of the present invention may be provided in any forms such as dried form, solution form, spread or impregnated form on carrier, etc.

The method for the measurement of D-sorbitol using the reagent for measuring of D-sorbitol according to the invention is carried out by adding a sample containing D-sorbitol to the reagent and measuring the change in the absorbance or fluorescence intensity. The reaction may be initiated by addition of any one or more of the components such as the sample, sorbitol dehydrogenase, or the coenzyme, and the measurement of absorbance or fluorescence intensity may be carried out at the termination of the reaction or at any time during the reaction. The sample containing D-sorbitol is not particularly limited and examples thereof include various clinical samples such as blood, urine, etc., various foods, etc.

A sample containing D-sorbitol is added to the above described reagent for determination of D-sorbitol preferably at a temperature of from 25° C. to 40° C. The reaction time may be appropriately set depending on the reaction temperature, the amount of sorbitol in the sample, the amount of enzyme contained in the reagent, etc., and usually within 10 minutes, preferably within 3 minutes.

The present invention will be further described in the following Examples, but the present invention should not be construed as being limited thereto.

All parts, percentages, ratios, etc. are by weight.

EXAMPLE 1

Into a 30-l jar fermenter was charged 18 l of a culture medium with pH 7.0 containing 2.0% (by weight, the same shall apply hereinafter) of D-sorbitol, 0.5% of peptone, 0.5% of yeast extract and 0.1% of dipotassium hydrogenphosphate. The culture medium was then sterilized at a temperature of 121° C. for 15 minutes. *Flavimonas oryzihabitans* A-520 strain (FERM BP-7195) was then inoculated with the culture medium. Incubation was then effected at a temperature of 30° C. with stirring at 200 rpm while being aerated at 1 vvm for 70 hours. The culture medium was then subjected to centrifugal separation to obtain about 300 g of wet bacterial cells. The bacterium thus obtained was then stored frozen. Subsequently, the: frozen bacterium was suspended in 2 l of a 50 mM Tris-HCl buffer (pH 7.5) containing 1 mM of phenylmethanesulfonyl fluoride (PMSF), 2 mM of EDTA and 2 mM of 2-mercaaptoethanol. The bacterium was then crushed by a French press. The bacterium thus crushed was then subjected to centrifugal separation to remove cell fragments. Thus, a crude enzyme solution containing a sorbitol dehydrogenase was obtained. The crude enzyme solution was then passed through a DEAE-Sepharose-FF column (produced by Pharmacia Corporation) which had previously been equilibrated with a 25 mM phosphate buffer (pH 8.0) containing 2 mM of EDTA and 2 mM of 2-mercaptoethanol and elution was carried out at a linear gradient of from 0 to 0.65 M KCl. Thus, a sorbitol dehydrogenase active fraction was obtained at a KCl concentration of from about 0.20 to 0.25 M. Subsequently, ammonium sulfate was added to the fraction thus obtained to a concentration of 20%. The fraction was then passed through Butyl Toyopearl Column (produced by TOSOH CORP.) equilibrated with 25 mM of phosphate buffer (pH 8.0) containing a 20% ammonium sulfate, 2 mM of EDTA and 2 mM of 2-mercaptoethanol. Elution was effected while the concentration of ammonium sulfate in the buffer was being gradually lowered. As a result, a sorbitol dehydrogenase active fraction was obtained at an ammonium sulfate concentration of from about 4% to 7%. The active fraction thus obtained was subjected to dialysis, and then passed through a DEAE-trisacryl column (produced by Pharmacia Corporation) which had previously been equilibrated with a 25 mM phosphate buffer (pH 8.0) containing 2 mM of EDTA and 2 mM of 2-mercaptoethanol so that it was eluted at a linear gradient of from 0 to 0.25 M KCl. Thus, a sorbitol dehydrogenase active fraction was obtained at a KCl concentration of from about 0.15 to 0.2 M. Subsequently, to the fraction thus obtained, ammonium sulfate was added to a concentration of 5%. The fraction was then passed through a Phenylcellulofine Column (produced by Pharmacia Corporation) equilibrated with a 25 mM phosphate buffer (pH 8.0) containing 2 mM of 5% ammonium sulfate, 2 mM EDTA and. 2 mM 2-mercaptoethanol. Elution was effected while the concentration of ammonium sulfate in the buffer was gradually lowered. As a result, a sorbitol dehydrogenase active fraction was obtained at an ammonium sulfate concentration of from about 2% to 1%. The yield of the sorbitol dehydrogenase thus obtained was about 40%. The sorbitol dehydrogenase thus obtained exhibited a specific activity of about 33 units per mg of enzyme protein. The degree of purification of the sorbitol dehydrogenase thus obtained was about 370 times that of the crude enzyme solution. The sorbitol dehydrogenase thus obtained had the foregoing physicochemical properties.

EXAMPLE 2

By a method similar to that described in Example 1, *Pseudomonas fluorescens* A-989 strain was cultured to obtain about 210 g of wet bacterial cells. The bacterium thus obtained was then stored frozen. Subsequently, a crude enzyme solution containing a sorbitol dehydrogenase was obtained by a method similar to that described in Example 1. The crude enzyme solution was then passed through a DEAE-Sepharose-FF column (produced by Pharmacia Corporation) which had previously been equilibrated with a 25 mM phosphate buffer (pH 8.0) containing 2 mM of EDTA and 2 mM of 2-mercaptoethanol. As a result, almost no sorbitol dehydrogenase was absorbed by the column. Sorbitol dehydrogenase in the unabsorbed fractions was recovered and ammonium sulfate was added to a concentration of 10%. The fraction was then passed through Butyl Toyopearl Column (produced by TOSOH CORP.) equilibrated with 25 mM of phosphate buffer (pH 8.0) containing a 10% ammonium sulfate, 2 mM of EDTA and 2 mM of 2-mercaptoethanol. Elution was effected while the concentration of ammonium sulfate in the buffer was gradually lowered. As a result,: a sorbitol dehydrogenase active fraction was obtained at an ammonium sulfate concentration of from about 4% to 3%. The active fraction thus obtained was passed through a Butyl Toyopearl Column (produced by TOSOH CORP.) equilibrated with the buffer (pH 8.0) and elution was effected while the concentration of ammonium sulfate in the buffer was gradually lowered. As a result, a sorbitol dehydrogenase active fraction was obtained at an ammonium sulfate concentration of from about 4% to 3%. The yield of the sorbitol dehydrogenase thus obtained was about 56%. The sorbitol dehydrogenase thus obtained exhibited a specific activity of about 4 units per mg of enzyme protein. The degree of purification of the sorbitol dehydrogenase thus obtained was about 110 times that of the crude enzyme solution. The sorbitol dehydrogenase thus obtained had the foregoing physicochemical properties.

EXAMPLE 3

By a method similar to that described in Example 1, *Pseudomonas fluorescens* A-654 strain was cultured to obtain about 300 g of wet bacterial cells. The bacterium thus obtained was then stored frozen. Subsequently, a crude enzyme solution containing a sorbitol dehydrogenase was obtained by a method similar to that described in Example 1. The crude enzyme solution was then passed through a DEAE-Sepharose-FF column (produced by Pharmacia Corporation) which had previously been equilibrated with a 25 mM phosphate buffer (pH 8.0) containing 2 mM of EDTA and 2 mM of 2-mercaptoethanol, and elution was carried out at a linear gradient of from 0 to 0.6 M KCl. Thus, a sorbitol dehydrogenase active fraction was obtained at a KCl concentration of from about 0.20 to 0.25 M. Subsequently, to the fraction thus obtained, ammonium sulfate was added to a concentration of 20%. The fraction was then passed through a Butyl Toyopearl Column (produced by TOSOH CORP.) equilibrated with a 25 mM phosphate buffer (pH 8.0) containing 20% ammonium sulfate, 2 mM EDTA and 2 mM 2-mercaptoethanol. Elution was effected while the concentration of ammonium sulfate in the buffer was gradually lowered. As a result, a sorbitol dehydrogenase active fraction was obtained at an ammonium sulfate concentration of from about 2% to 1%. The fraction was then passed through a Red Sepharose Column (produced by Pharmacia Corporation) equilibrated with a 25 mM phosphate buffer (pH 8.0) containing 2 mM EDTA and 2 mM 2-mercaptoethanol. Elution was effected with 2 mM NADH to obtain a sorbitol dehydrogenase active fraction. The yield of the sorbitol dehydrogenase thus obtained was about 17%. The sorbitol dehydrogenase thus obtained exhibited a specific activity of about 25 units per mg of enzyme protein. The degree of purification of the sorbitol dehydrogenase thus obtained was about 1,130 times that of the crude enzyme solution. The sorbitol dehydrogenase thus obtained had the foregoing physicochemical properties.

EXAMPLE 4

Using the sorbitol dehydrogenase derived from *Flavimonas oryzihabitans* A-520 strain purified in Example 1, a reagent for the quantitative determination of sorbitol having the following composition was prepared.

| Tris-HCl buffer (pH 9.0) | 100 mM |
| NAD$^+$ (produced by Oriental Yeast Co., Ltd.) | 2.5 mM |
| Enzyme described above | 2.5 U/ml |

Figure 13:
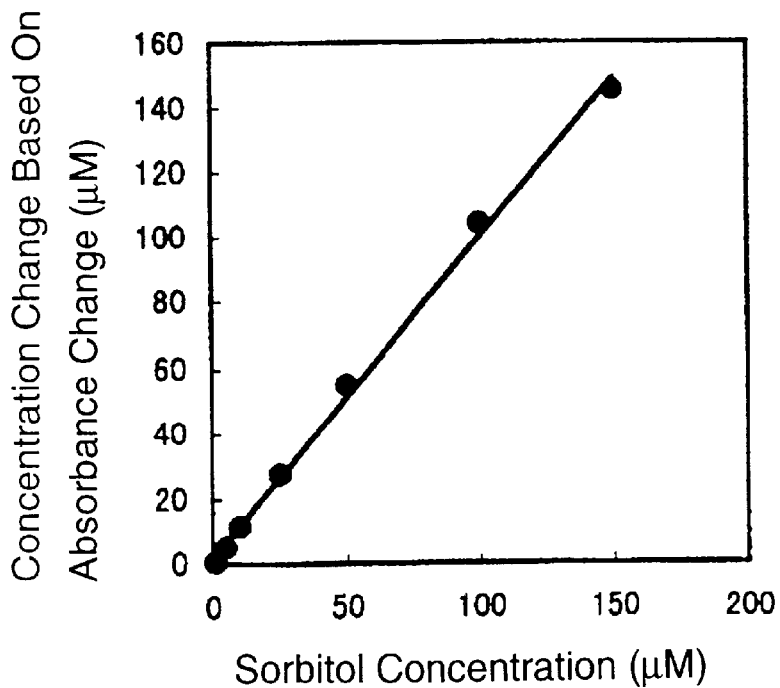
FIG. 13 is a graph illustrating the results of measurement of D-sorbitol concentration using a reagent for the quantitative determination of D-sorbitol prepared from a sorbitol dehydrogenase of the present invention.

0.8 ml of the reagent for the quantitative determination of sorbitol was then subjected to plain incubation at a temperature of 37° C. for 5 minutes. To the reagent were each then added 0.2 ml of various samples of. D-sorbitol standard product (first grade, produced by NACALAI TESQUE, INC.) which had been adjusted to 5 $\mu$m, 25 $\mu$m, 40 $\mu$m, 125 $\mu$m, 250 $\mu$m, 400 $\mu$m and 750 $\mu$m, respectively. These samples were each then allowed to undergo reaction at a temperature of 37° C. in a Type UV-265 spectrophotometer produced by Shimadzu Corp. for 30 minutes. The absorbance was then determined at 340 nm. The blank value of distilled water instead of the foregoing sample was then subtracted from the value thus determined to determine the change of absorbance ($\Delta$OD). There was a linear relationship between the concentration calculated from the change of absorbance and the molecular absorptivity of NAD$^+$ (6,220 M$^{-1}$cm$^{-1}$) and the content of D-sorbitol. FIG. 13 is a scatter diagram illustrating the relationship between the actual D-sorbitol concentration and the D-sorbitol concentration measured with the foregoing reagent. The equation of a regression line obtained by linear approximation using the method of least squares is y=−0.98x+2.1 (r=0.998). The coefficient of x and the coefficient of correlation are almost equal to 1. Accordingly, it can be seen that D-sorbitol in the sample can be accurately determined using the foregoing reagent.

EXAMPLE 5

Using the sorbitol dehydrogenase derived from *Flavimonas oryzihabitans* A-520 strain purified in Example 1, a reagent for the quantitative determination of sorbitol having the following composition was prepared.

| Tris-HCl buffer (pH 9.0) | 80 mM |
|---|---|
| NAD+ (produced by Oriental Yeast Co., Ltd.) | 2.0 mM |
| Enzyme described above | 5 U/ml |
| WST-8 | 1 mM |
| Diaholase | 2 U/ml |

0.78 ml of the reagent for the quantitative determination of sorbitol was then subjected to plain incubation at a temperature of 30° C. for 5 minutes. To the reagent were each then added 0.02 ml of various samples of D-sorbitol standard product (first grade, produced by NACALAI TESQUE, INC.) which had been adjusted to 1 μm, 5 μm, 20 μm, 80 μm and 320 μm, respectively. These samples were each then allowed to undergo reaction at a temperature of 30° C. in a Type UV-265 spectrophotometer produced by Shimadzu Corp. for 6 minutes. The absorbance was then determined at 460 nm. The blank value of distilled water instead of the foregoing sample was then subtracted from the value thus determined to determine the change of absorbance (ΔOD). There was little or no ΔOD change after 3 minutes from the beginning of the reaction, demonstrating that the reaction was terminated in 3 minutes. There was a linear relationship between the concentration calculated from the molecular absorptivity coefficient of WST-8 (30,000 $M^{-1}cm^{-1}$) on the basis of ΔOD determined 30 minutes, after the beginning of the reaction and the concentration, of D-sorbitol added to the reaction solution.

Figure 14:
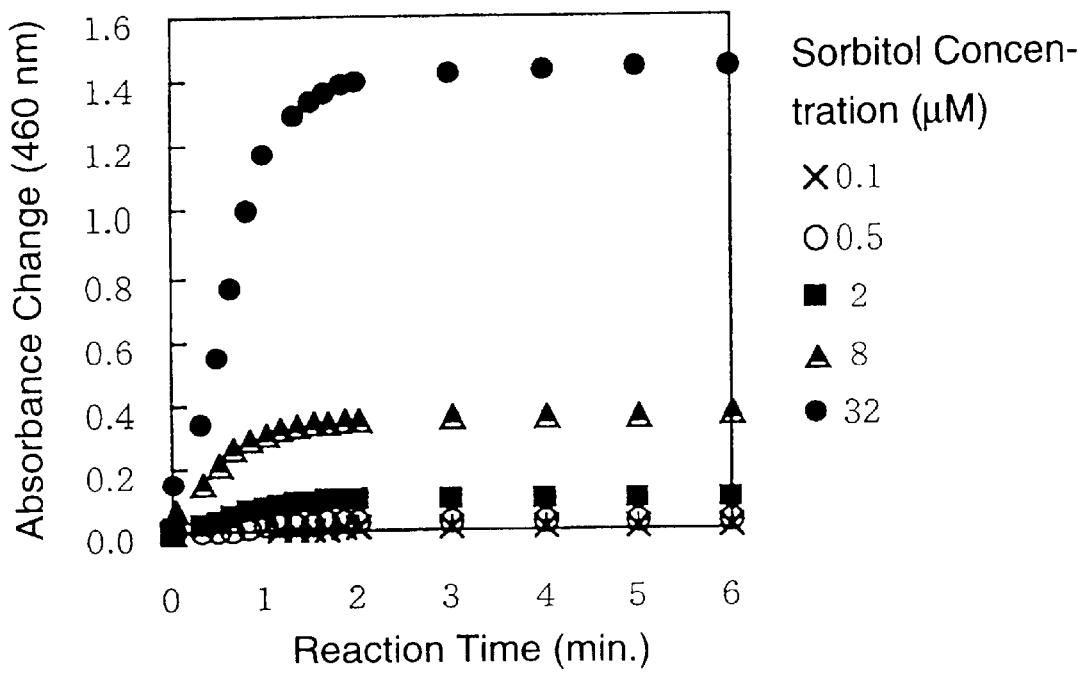
FIG. 14 is a graph illustrating the progress of reaction by a reagent for the quantitative determination of D-sorbitol prepared from a sorbitol dehydrogenase of the present invention.

FIG. 14 is a graph illustrating the relationship between the reaction time and ΔOD. As can be seen in FIG. 6, the reaction ends in 3 minutes.

Figure 15:
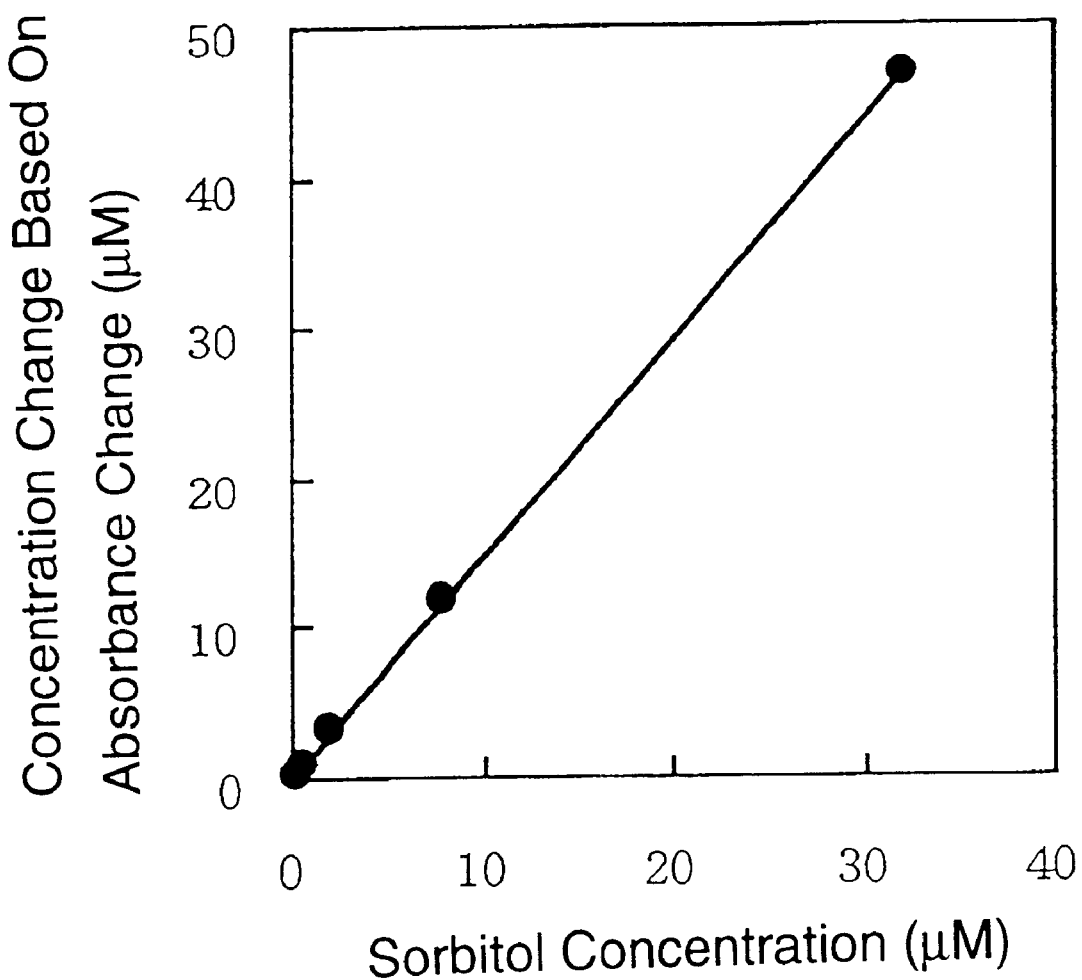
FIG. 15 is a graph illustrating the results of measurement of D-sorbitol concentration using a reagent for the quantitative determination of D-sorbitol prepared from a sorbitol dehydrogenase of the present invention.

FIG. 15 is a scatter diagram illustrating the relationship between the concentration of D-sorbitol added to the reaction solution and the D-sorbitol concentration measured with the foregoing reagent. The equation of a regression line obtained by linear approximation using the method of least squares is y=1.45x+0.2 (r=1.000). The coefficient of x and the coefficient of correlation are almost equal to 1. Accordingly, it can be seen that D-sorbitol in the sample can be accurately determined up to 1 μm using the foregoing reagent.

While the invention has been described in detail and with reference to specific embodiments thereof, it will be apparent to one skilled in the art that various changes and modifications can be made therein without-departing from the spirit and scope thereof.

This application is based on Japanese patent application No. Hei. 11-238284 filed on Aug. 25, 1999, incorporated herein by reference in its entirety.

What is claimed is:

1. A sorbitol dehydrogenase having the following physicochemical properties:

(1) activity: the sorbitol dehydrogenase catalyzes dehydrogenation oxidation of D-sorbitol in the presence of $NAD^+$ to produce D-fructose, and catalyzes a reverse reaction which reduces D-fructose in the presence of NADH to produce D-sorbitol and $NAD^+$;

(2) substrate specificity: the sorbitol dehydrogenase exhibits a Vmax/Km value of about 40 or less for galactitol and about 3 or less for L-iditol when the Vmax/Km value for D-sorbitol is taken as 100, and which does not act on D-arabitol, D-mannitol, xylitol and D-glucose; and (3) exhibits a Km value of about 6 mM or less with respect to D-sorbitol.

2. The sorbitol dehydrogenase as claimed in claim 1, which exhibits a Km value of about 4 mM or less with respect to D-sorbitol.

3. The sorbitol dehydrogenase as claimed in claim 1, which is derived from a microorganism belonging to the genus Flavimonas or Pseudomonas.

4. The sorbitol dehydrogenase as claimed in claim 1, which is derived from *Flavimonas oryzihabitans* or *Pseudomonas fluorescens*.

5. The sorbitol dehydrogenase as claimed in claim 1, which is derived from *Flavimonas oryzihabitans* A-520 deposited with National Institute of Bioscience and Human Technology, Ministry of International Trade and Industry with Accession No. FERM BP-7195.

6. A microorganism belonging to the genus Flavimonas or Pseudomonas which is capable of producing a sorbitol dehydrogenase as claimed in claim 1.

7. A process for the production of a sorbitol dehydrogenase as claimed in claim 1, which comprises culturing a microorganism belonging to the genus Flavimonas or Pseudomonas capable of producing said sorbitol dehydrogenase in a culture medium, and then collecting a sorbitol dehydrogenase from the culture.

8. A process for the measurement of sorbitol which comprises adding a composition containing a sorbitol dehydrogenase as claimed in claim 1 to a sample to cause reaction, and then measuring the content of sorbitol in said sample.

9. A reagent for the quantitative determination of sorbitol, which comprises a sorbitol dehydrogenase as claimed in claim 1, $NAD^+$ and a buffer.

* * * * *